United States Patent [19]
Riza

[11] Patent Number: 5,716,369
[45] Date of Patent: Feb. 10, 1998

[54] APPARATUS FACILITATING SUTURING IN LAPAROSCOPIC SURGERY

[76] Inventor: Erol D. Riza, 550 Riverside Dr., Rossford, Ohio 43460

[21] Appl. No.: 728,268

[22] Filed: Oct. 8, 1996

Related U.S. Application Data

[63] Continuation-in-part of Ser. No. 217,613, Mar. 25, 1994, Pat. No. 5,562,688.

[51] Int. Cl.⁶ .................................................. A61B 17/04
[52] U.S. Cl. ........................... 606/148; 606/139; 606/144
[58] Field of Search ................................. 606/139, 144, 606/148, 149

[56] References Cited

U.S. PATENT DOCUMENTS

| | | |
|---|---|---|
| 2,108,206 | 1/1938 | Meeker . |
| 4,535,773 | 8/1985 | Yoon . |
| 4,553,543 | 11/1985 | Amarasinghe . |
| 4,601,710 | 7/1986 | Moll . |
| 4,911,164 | 3/1990 | Roth . |
| 4,968,315 | 11/1990 | Gatturna . |
| 5,009,643 | 4/1991 | Reich et al. . |
| 5,084,058 | 1/1992 | Li . |
| 5,087,263 | 2/1992 | Li . |
| 5,176,691 | 1/1993 | Pierce . |
| 5,217,441 | 6/1993 | Shichman . |
| 5,234,444 | 8/1993 | Christoudias . |
| 5,320,629 | 6/1994 | Noda et al. . |
| 5,324,298 | 6/1994 | Phillips . |
| 5,334,200 | 8/1994 | Johnson ........................... 606/148 |
| 5,354,298 | 10/1994 | Lee et al. ........................ 606/139 |
| 5,391,174 | 2/1995 | Weston ............................ 606/148 |
| 5,501,692 | 3/1996 | Riza . |
| 5,507,758 | 4/1996 | Thomason et al. ............ 606/148 |
| 5,540,704 | 7/1996 | Gordon et al. ................. 606/144 |
| 5,562,688 | 10/1996 | Riza . |

FOREIGN PATENT DOCUMENTS

| | | |
|---|---|---|
| 5324298 | 6/1994 | U.S.S.R. . |

*Primary Examiner*—William E. Kamm
*Assistant Examiner*—Carl H. Layno
*Attorney, Agent, or Firm*—Mac Millan, Sobanski & Todd

[57] ABSTRACT

A plug for use in minimally invasive surgery which includes recesses for facilitating suturing of a trocar insertion site. The plug may be inserted in an axial bore of a separate gripper housing, and fixed in place by the gripping structure of the housing or a first end of the plug may be inserted directly into the trocar insertion site after a trocar is removed. The plug is provided with a pair of opposed, longitudinally extending recesses formed in the outer surface thereof. Each recess extends from a second end of the plug to a point between the first end and the second end of the plug. The recess may cooperate to form a single slot in the plug defined by a pair of axially extending arms. The plug is also provided with reinforcing segments which extend between the arms for stabilization.

19 Claims, 10 Drawing Sheets

APPARATUS FACILITATING SUTURING IN LAPAROSCOPIC SURGERY

CROSS REFERENCE TO RELATED APPLICATION

This is a continuation-in-part of my prior application Ser. No. 08/217,613, filed Mar. 25, 1994, issuing as U.S. Pat. No. 5,562,688 on Oct. 8, 1996.

BACKGROUND OF THE INVENTION

This invention relates in general to surgical instruments and in particular to an improved structure for a gripper for trocars used in minimally invasive surgical procedures, such as laparoscopic surgical procedures, and a plug for use therewith which facilitates suturing of laparoscopic surgery puncture wounds.

Trocars are sharp-pointed instruments used to puncture a body cavity. This is often done so that fluids may be drained using a tube inserted into the opening. Trocars are also used in laparoscopic surgery. Laparoscopic surgery is a relatively new operating technique which involves puncturing the abdominal wall, and then performing the surgery through the relatively small opening of the puncture. This technique is much less invasive than conventional surgery in which the surgery is performed through a relatively large incision through the abdominal wall.

Before puncturing the abdominal wall, an inert gas, such as carbon dioxide, is introduced within the abdominal cavity, usually by means of a needle supplied with the inert gas from a pressurized source. The introduction of the inert gas expands the abdomen to facilitate access to the body parts requiring surgery and visual observation of the procedure.

Trocars used in laparoscopic surgery generally include a stylet having a sharp tip for penetrating through a patient's abdominal wall and a hollow trocar guide tube having smooth internal and external surfaces. Prior to use, the trocar stylet is inserted into the trocar guide tube. After the abdomen has been expanded by introduction of the inert gas, the trocar is used to puncture the abdominal wall. Typically, a small incision is made in the skin at a selected site, using a scalpel. The sharp point of the stylet is inserted into the incision, and then pressed through the abdominal wall. After the trocar has punctured the abdominal wall, the stylet is removed, leaving the trocar guide tube extending through the abdominal wall. A variety of surgical instruments may then be inserted through the trocar guide tube to perform the surgery within the abdomen.

As indicated above, the trocar guide tube typically has a smooth external surface so that it will slide relatively easily into the puncture. However, the smooth surface does not grip the abdominal wall well once it has been inserted. Therefore the trocar guide tube may be accidentally pulled out of the puncture during removal of surgical instruments, or may be expelled by gas pressure within the abdomen. A gripper is therefore commonly used to hold the trocar guide tube in position relative to the abdominal wall.

One general type of gripper which is known is a hollow cylindrical device which has an external helical thread and structure for releasably gripping an associated trocar guide tube. The trocar guide tube is inserted into the gripper before the trocar is used to puncture the abdominal wall. After the trocar has penetrated the abdominal wall, the gripper is slid down the trocar guide tube into contact with the abdominal wall. The gripper is then rotated to thread the gripper into the abdominal wall, fixing the gripper against axial movement. The gripping structure is then operated to secure the trocar guide tube against axial movement within the gripper.

As indicated above, laparoscopic surgery is much less invasive than conventional surgical techniques, and much smaller openings are made through the abdominal wall. It had been thought, up to now, that the puncture wounds thus created did not need to be sutured to heal properly, given their relatively small size. Nevertheless, it has been found that the punctures made through the abdominal wall, particularly of the larger diameter trocars, sometimes do not close properly. Wound closure of the fascia layer or layers of the abdominal wall is especially important. Without proper wound closure, hernias can develop at these sites when portions of internal organs, notably bowel, protrude through the wound. However, the relatively small size of the wound makes suturing of the fascia using conventional suturing techniques difficult. Therefore, an apparatus that facilitates the suturing of puncture wounds resulting from laparoscopic surgery, thus facilitating wound closure, would be desirable.

BRIEF SUMMARY OF THE INVENTION

This invention relates to a trocar gripper with means for facilitating suturing of an insertion site thereof. The gripper includes a tubular housing having a circumferential flange formed thereabout. The housing is provided with gripping structure for gripping a trocar guide tube which may be inserted through the axial bore of the tubular housing. The housing is also provided with structure for fixing the axial position of the housing within an incision in a patient. A pair of opposed openings are formed through the tubular wall of the housing into the axial bore thereof, intermediate the first end thereof and the circumferential flange. A pair of locating notches are formed in the axial face of a second end of the housing.

The invention also includes a plug which may be inserted the axial bore of the gripper from the second end of the housing, and fixed in place by the gripping structure of the housing. The plug is provided with an elastomeric seal on a first end thereof which engages the surface of the bore of the housing. The plug is provided with a pair of parallel arms extending axially from a second end of the plug. Each parallel arm has a radially outwardly extending lug formed thereon. Each lug is seated in a respective locating notch on the second end of the housing to rotationally orient the plug within the housing. The plug also includes a pair of opposed inclined slots formed on the outer surface of the second end of the plug, between the axially extending arms. When the plug is inserted into the housing, and the lugs thereof seated within the locating notches of the housing, each inclined slot extends from the second end of the plug to a point adjacent the associated opening through the wall of the housing. An axial bore may be provided through the plug to permit the insertion of laparoscopic surgical instruments with the plug in place.

Various objects and advantages of this invention will become apparent to those skilled in the art from the following detailed description of the preferred embodiment, when read in light of the accompanying drawings.

DETAILED DESCRIPTION OF THE INVENTION

Figure 1:
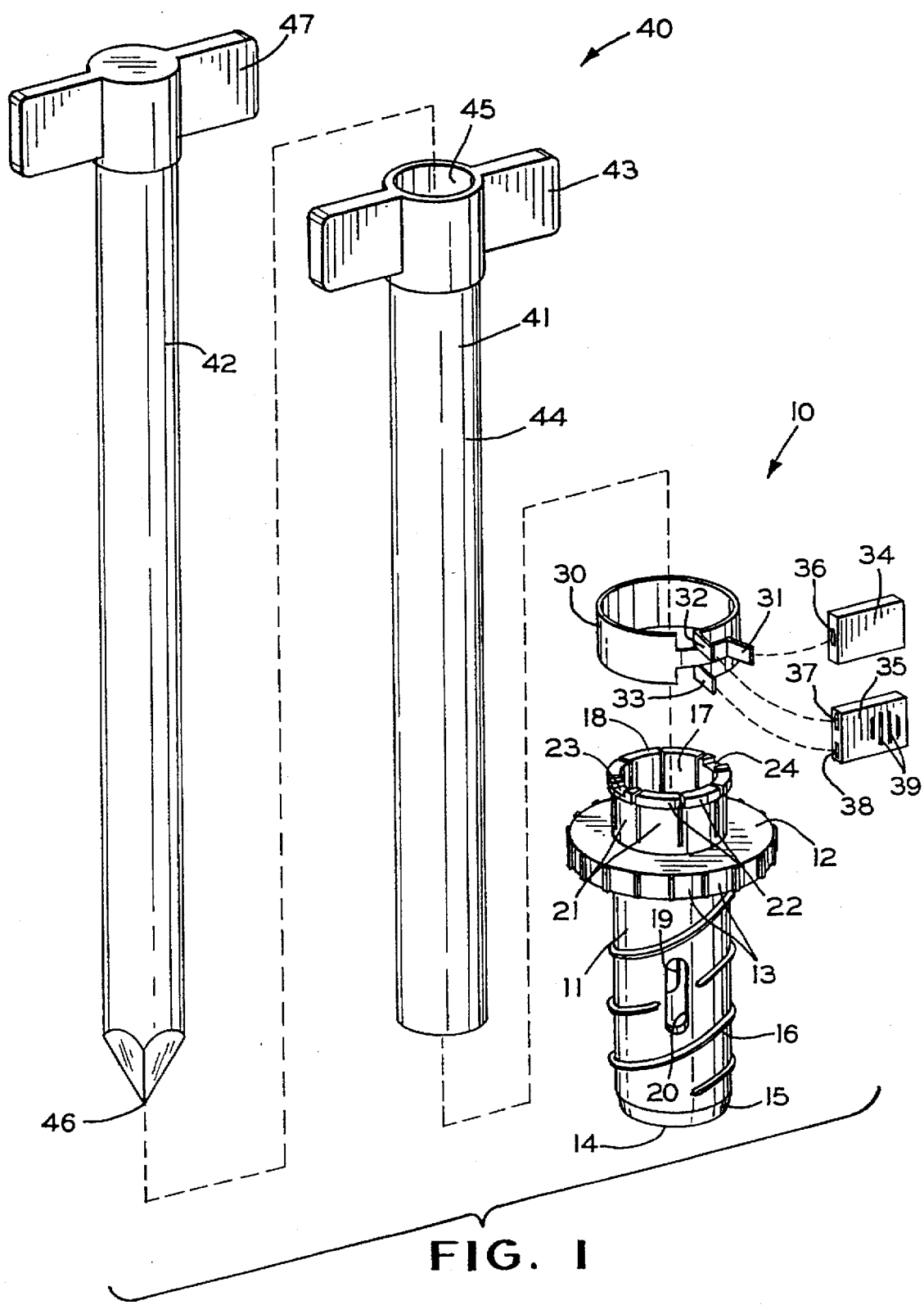
FIG. 1 is an exploded perspective view of the gripper in accordance with this invention with the stylet and guide tube of a typical trocar.

Referring now to the drawings, there is illustrated in FIG. 1 a trocar gripper, indicated generally at 10, in accordance with this invention. The gripper 10 includes a tubular housing 11 which is formed having a circumferential flange 12 formed thereabout. The flange 12 is preferably formed with axially extending ribs 13 formed on the outer periphery thereof. As will be explained further below, the ribs 13 provide a relatively non-slip surface for rotating the housing 11 about the axis thereof.

A distal first end 14 of the housing 11 is provided with an inwardly tapered portion 15 which eases insertion of the housing 11 into a patient. The housing 11 is formed with a helical thread 16 on the exterior surface thereof, extending between the flange 12 and the tapered portion 15 at the first end 14 of the housing 11. The helical thread 16 forms an engaging member operatively coupled to the housing 11 for selectively fixing the axial position of the first end 14 of the housing 11 within an incision in a patient.

Figure 3:
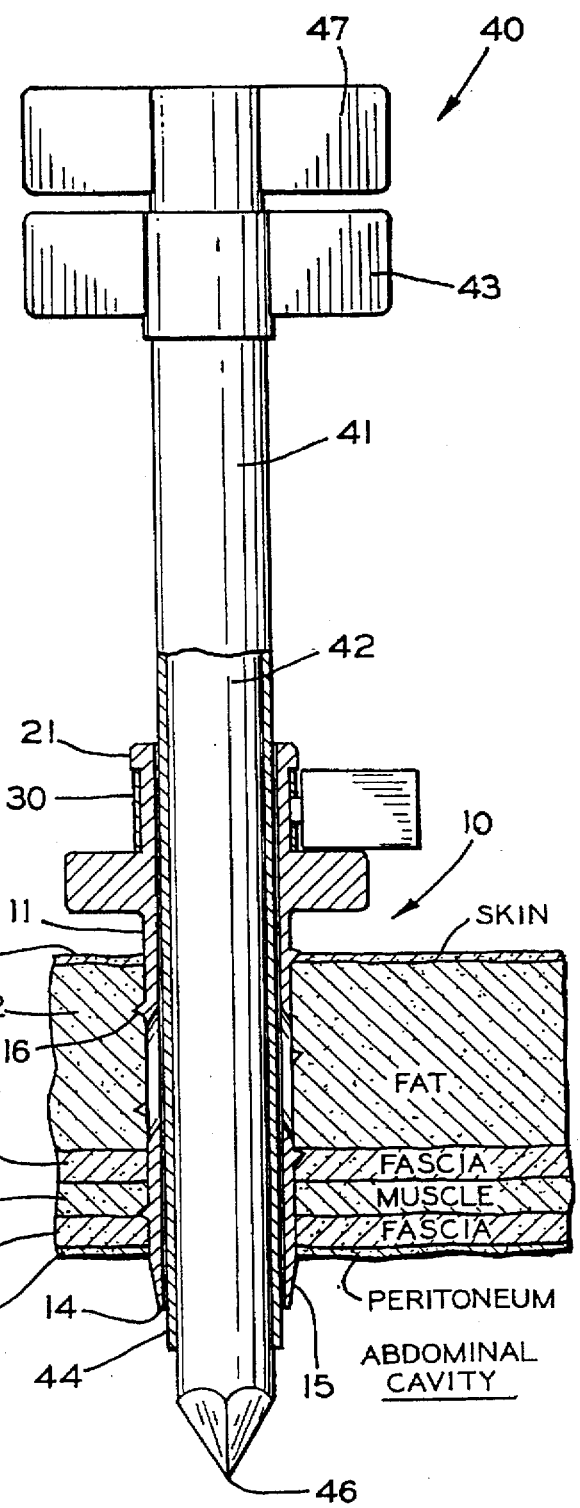
FIG. 3 is a side elevational view similar to FIG. 2, partly broken away, wherein the gripper and trocar are shown inserted into the abdominal wall of a patient with the gripper shown in a second axial position relative to the trocar.
Figure 5:
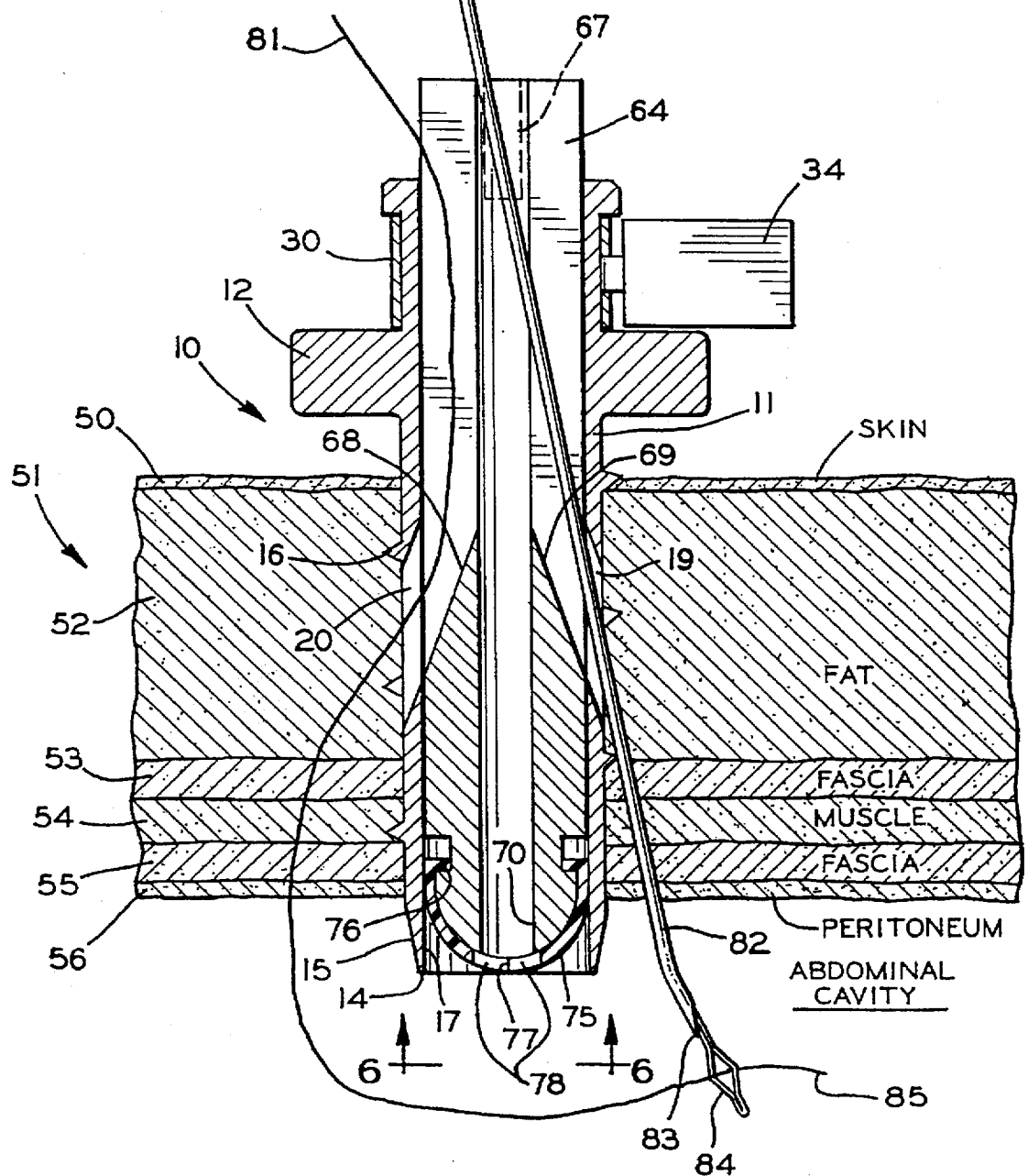
FIG. 5 is a sectional elevational view of the plug and gripper illustrated in FIG. 4, wherein the plug is installed in the gripper, illustrating a means of suturing the insertion site of the gripper.

The tubular housing 11 defines an axial bore 17 extending from the first end 14 to a proximal second end 18 thereof. Intermediate the first end 14 and the flange 12, a pair of opposed openings 19 and 20 are formed through the tubular wall of the housing 11 into the axial bore 17 thereof. As is best seen in FIGS. 3 and 5, the openings 19 and 20 are preferably inclined outwardly at an acute angle to the axis defined by the bore 17, in the direction of the first end 14. The purpose of the openings 19 and 20 will be explained below.

A plurality of axially extending gripping members or fingers 21 are formed on the second end 18 of the housing 11. Each finger 21 is formed with an outwardly extending lip 22 at the free end thereof. The purpose of the fingers 21 and of the lips 22 will be explained below. Two locating notches 23 and 24 are formed on the axial face of the second end 18 of the housing 11, on the ends of selected ones of the fingers 21. The purpose of the locating notches 23 and 24 will be explained below. Preferably, the entire housing 11 is formed from a molded plastic material.

The gripper 10 also includes a clamp 30, which is preferably formed of a spring steel. The clamp 30 is formed into a circular shape, with a first end having a single radially outwardly extending tab 31. A second end of the clamp is split so as to extend on either side of the first end. One portion of the second end is formed into a radially outwardly extending tab 32, while the other portion of the second end is similarly formed into a radially outwardly extending tab 33. The diameter of the clamp 30, as is known, may be expanded by squeezing the tab 31 toward the tabs 32 and 33 of the second end. To facilitate gripping the tabs 31, 32, and 33, a pair of finger pads 34 and 35 are provided. The finger pad 34 has a central opening 36 which receives the tab 31. The finger pad 35 has a pair of openings 37 and 38 which receive respective tabs 32 and 33. The tabs 31, 32 and 33 may be press fit into respective openings 36, 37 and 38, or may be joined to the clamp 30 by any other suitable method, such as by a suitable adhesive. The finger pads 34 and 35 are preferably formed from a molded plastic material. If desired, the finger pads 34 and 35 may be formed with relatively non-slip surfaces, such as that provided by the parallel ribs 39 illustrated on the pad 35.

The clamp 30 is assembled onto the second end 18 of the housing 11, as is illustrated in FIGS. 2 through 5, encircling the fingers 21. The clamp 30, in a relaxed state, defines an inner diameter slightly less than an outer diameter defined by the fingers 21. Thus, the each of the fingers 21 will normally be urged to bend radially inwardly by the clamp 30 when the clamp 30 is in a relaxed state. The clamp 30 is retained on the fingers 21 by the flange 12 and the outwardly extending lip 22 on the end of each finger 21.

The gripper 10 is adapted to receive a conventional trocar, indicated generally at 40, within the axial bore 17 of the housing 11. The trocar 40 includes a trocar guide tube 41 and a stylet 42. The trocar guide tube 41 includes a handle 43 for manipulating a sleeve portion 44 of the trocar guide tube 41. The sleeve portion 44 defines a bore 45 extending'axially through the trocar guide tube 41. The stylet 42 is a solid rod having a sharp point 46 on a one end, and a handle 47 for manipulating the stylet 42 on the other end. Of course, those with ordinary skill in the art will recognize that the conventional trocar 40 may be'formed other than as specifically described and illustrated.

Figure 2:
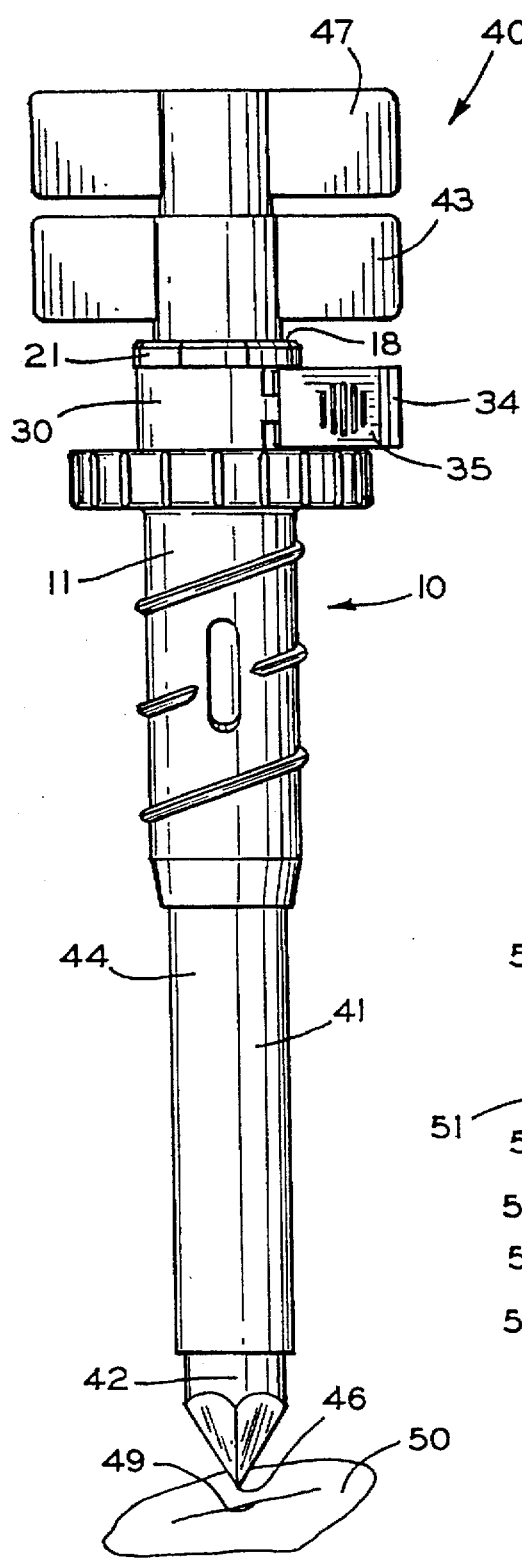
FIG. 2 is a side elevational view of the gripper and trocar illustrated in FIG. 1, wherein the gripper is shown assembled onto the trocar in a first axial position relative to the trocar, prior to insertion into the abdominal wall of a patient.

Referring now to FIG. 2, to assemble the gripper 10 onto the trocar 40, the user (not shown) urges the finger pads 34 and 35 of the clamp 30 toward one another to expand the clamp 30. This permits the fingers 21 of the housing 11 to flex radially outwardly to their axially extending, unbiased positions. In this condition, the inner diameter defined by the fingers 21 is slightly larger than the outer diameter of the sleeve portion 44 of the trocar guide tube 41. The sleeve portion 44 of the trocar guide tube 41 is inserted into the axial bore 17 (FIG. 1) of the housing 11 from the second end 18 of the housing 11. The finger pads 34 and 35 of the clamp 30 are released when the housing 11 of the gripper 10 is adjacent the handle 43 of the trocar guide tube 41. The clamp 30 contracts when the finger pads 34 and 35 are released, urging the fingers 21 of the housing 11 radially inward to grip the sleeve portion 44 of the trocar guide tube 41. The clamp 30 thus cooperates with the fingers 21 to fix the axial position of the gripper 10 relative to the trocar guide tube 41. The stylet 42 is inserted through the hollow trocar guide tube 41, until the handle 47 of the stylet 42 engages 42 engages the handle 43 of the trocar guide tube 41. The trocar 40 is then ready for insertion through the abdominal wall of a patient.

Before inserting the trocar 40, a small incision 49 is generally made through the patient's skin 50 at the desired insertion point. The point 46 of the stylet 42 is then inserted into the incision 49. The user (not shown) pushes with the handle 47 of the stylet 42 to urge the pointed end 46 of the stylet 42 through the abdominal wall 51 and into the abdominal cavity, as illustrated in FIG. 3.

The abdominal wall 51 is made of several layers of tissue. Generally, the layers will include, from the outermost to the innermost, the skin 50, a layer of fat 52, an outer layer of fascia 53, a layer of muscle 54, an inner layer of fascia 55, and the peritoneum 56. Of course, it is well known that in portions of the abdominal wall 51, only an inner layer of fascia 55 is present. It is also known that, while the thickness of the fat layer 52 may widely vary among individual adult patients, the combined thickness of the fascia layers 53 and 55, the muscle layer 54, and peritoneum 56 is relatively constant, being generally in the range of two centimeters thick.

The sleeve portion 44 of the trocar guide tube 41 is driven through the abdominal wall 51 along with the stylet 42. To prevent the trocar guide tube 41 from being expelled from the puncture by gas pressure, or accidentally pulled from the puncture when withdrawing a surgical instrument, it is known to employ a trocar gripper to engage both the abdominal wall 51 and the trocar guide tube 41. The gripper 10 is thus employed by first loosening the clamp 30. This permits the housing 11 of the gripper 10 to be moved axially along the sleeve portion 44 of the trocar guide tube 41 and into contact with the skin 50 of the patient. The clamp 30 is released, causing the fingers 21 of the gripper 10 to be urged radially inward to grip the trocar guide tube 41. The handle 43 of the trocar guide tube 41 is then rotated and pressed toward the abdominal wall 51, causing the gripper 10 to rotate and move inwardly therewith. In this manner, the helical thread 16 formed on the housing 11 engages and cooperates with the abdominal wall 51 to "screw" the housing 11 into the abdominal wall 51. The inwardly tapered portion 15 of the first end 14 of the housing 11 eases entry of the housing 11 into the abdominal wall 51. The gripper 10 is advanced through the abdominal wall 51 until the first end 14 of the housing 11 extends into the abdominal cavity by the desired amount, which is normally approximately one centimeter. If desired, a reference mark (not shown) such as a circumferential rib may be provided on the housing 11 the desired distance from the first end 14 thereof. Such a reference mark would provide a visual indication, using conventional laparoscopic viewing techniques, of proper positioning of the housing 11.

Alternatively, after the first end 14 of the housing 11 is positioned against the skin 50 the housing 11 may be urged into the puncture and rotated by grasping the flange 12 formed on the housing 11. This rotation of the housing 11 is facilitated by the raised ribs 12 provided on the flange 12 of the housing 11. The ribs 13 provide for increased frictional engagement by the fingers and thumb of the user (not shown) for accomplishing this rotational movement. The housing 11 is thus advanced through the abdominal wall 51 until the first end 14 thereof extends into the abdominal cavity by the desired amount, as described above.

After the gripper 10 is properly positioned within the abdominal wall, the clamp 30 can be expanded, thereby releasing the trocar guide tube 41, which may then be moved to a desired position relative to the gripper 10. Releasing the clamp 30 will cause the fingers 21 to again grip the trocar guide tube 41 in the manner described above, fixing the axial position of the trocar guide tube 41 relative to the gripper 10 and thus relative to the abdominal wall 51.

With the trocar guide tube 41 properly positioned relative to the abdominal wall 51, the stylet 42 is removed from the trocar guide tube 41. Elongated surgical instruments (not shown) may then be inserted into the abdomen through the trocar guide tube 41 to perform the laparoscopic surgery in a conventional manner.

Figure 4:
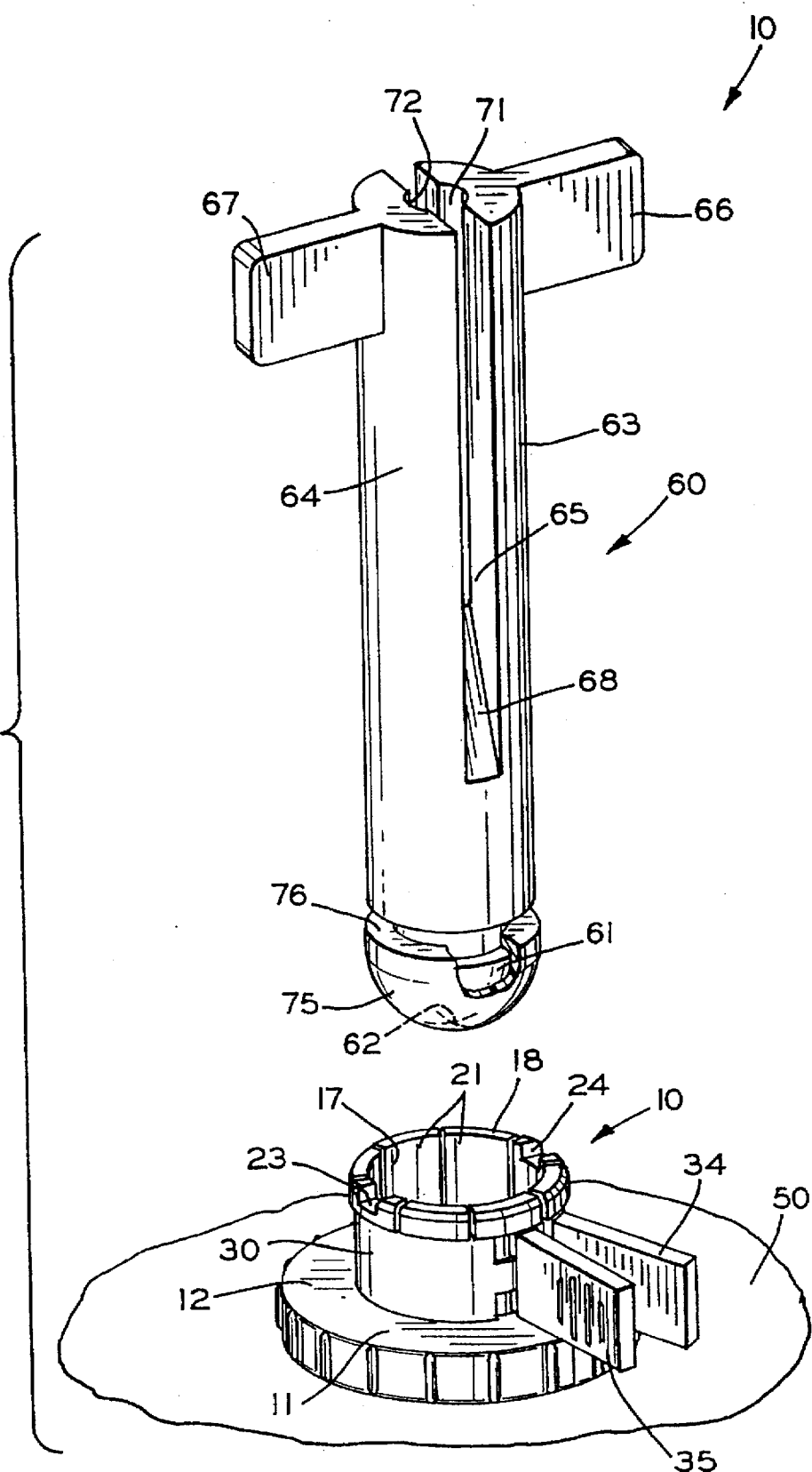
FIG. 4 is a perspective view, partly in section, of the gripper illustrated in FIGS. 1 through 3 after removal of the trocar and prior to insertion of a plug in accordance with this invention.

FIG. 4 illustrates a removable plug 60 which is designed to be used with the gripper 10. The plug 60 is generally cylindrical in construction and provided with a mushroom-shaped extension 61 on a first end 62 thereof. A pair of parallel arms 63 and 64 extend axially from the first end 61 of the plug 60. The arm 63 is provided with a radially outwardly extending lug 66 at the free end thereof. Similarly, the arm 64 is provided with a radially outwardly extending lug 67 at the free end thereof, the lug 66 extending in the opposite direction from the lug 67.

The plug 60 is provided with a pair of opposed inclined recesses 68 and 69 (shown in FIG. 5) formed in the outer surface of the second end 65 thereof. The recess 68 extends axially from the second end 65 of the plug 60, between the arms 63 and 64, to a point intermediate the first end 62 and the second end 65. The recess 68 is formed at an angle to the axis defined by the plug 60, and has a decreasing depth toward the first end 62. The recess 69 is formed on the opposite side of the plug 60 from the recess 68. The recess 69 is similarly outwardly sloped from the second end 65 of the plug 60 toward the first end 62 of the plug 60. The recess 69 extends axially from the second end 65 of the plug 60, between the arms 63 and 64, to a point intermediate the first end 62 and the second end 65. Preferably, the entire plug 60 is molded from a rigid plastic material.

In the preferred embodiment, an axial bore 70 (FIG. 5) is provided through the plug 60 from the first end 62 to the second end 64. A semi-circular groove 71 formed in the arm 63, and a similar semi-circular groove 72 formed in the arm 64 cooperate to define a diameter which is the same as that defined by the axial bore 70. As will be further explained below, the bore 70 and the grooves 71 and 72 permit small diameter surgical tools (not shown) to be passed through the plug 60.

Figure 6:
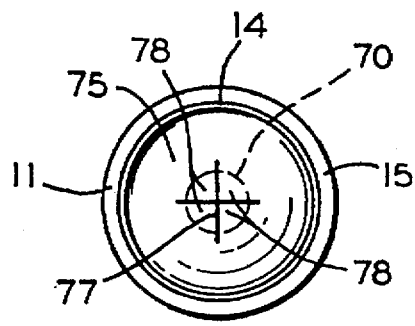
FIG. 6 is an end elevational view of the elastomeric seal of the plug illustrated in FIGS. 4 and 5.

The plug 60 is provided with an elastomeric seal 75, which may suitably be formed from latex rubber. The seal 75 is cup-shaped with an inwardly extending flange 76 formed about the rim thereof. The seal 75 is sized to fit over the mushroom-shaped extension 61 formed on the first end 62 of the plug 60, and is held in place thereon by the flange 76. As is best seen in FIG. 6, the seal 75 includes a central cross-shaped incision 77. The incision 77 divides the central portion of the seal 75 into four flaps 78 which resiliently cover the axial bore 70 through the plug 60 when the seal 75 is fitted over the mushroom-shaped extension 61 of the plug 60.

When the trocar guide tube 41 (FIG. 3) is removed from the housing 11, the plug 60 can be inserted into the axial bore 17 of the housing 11. The clamp 30 is expanded using the finger pads 34 and 35, and the trocar guide tube 41 is removed from the axial bore 17 of the housing 11. The plug 60 is then inserted into the axial bore 17 of the housing 11 from the second end 18 thereof. The lug 66 is seated in one of the locating notches 23 and 24 on the second end 18 of the housing 11. The lug 67 is seated in the other of the locating notches 23 and 24. In this manner, the plug 60 is rotationally and axially oriented within the housing 11 of the gripper 10. The clamp 30 is then released to cause the fingers 21 to grip and hold the plug 60 in the housing 11.

Referring now to FIG. 5, the seal 75 on the plug 60 engages the surface of the axial bore 17 through the gripper 10 between the first end 14 of the housing 11 and the opposed openings 19 and 20 through the tubular wall of the housing 11. Additionally the flaps 78 of the seal 75 cover the axial bore 70 through the plug 60. The seal 75 thus essentially seals the plug 60 to hold the inert gas within the abdominal cavity. A small amount of the gas may escape through the incision 77 through the seal 75, however this amount may easily be replaced from the gas supply (not shown) to keep the abdomen inflated.

As discussed above, the axial bore 70 of the plug 60 and the incision 77 in the seal 75 permit the insertion of relatively small diameter laparoscopic surgical instruments (not shown) into the abdominal cavity with the plug 60 installed. As the instruments are inserted through the incision 77, the flaps 78 of the seal 75 are bent downwardly and radially outwardly. When the instruments are removed, the flaps 78 resiliently return to cover the axial bore 70 through the plug 60, thus restricting the escape of gas from the abdominal cavity.

Another function of the gripper 10 is to facilitate the suturing of the fascia layers 53 and 55 of the abdominal wall 51. As is shown in FIG. 5, when the first end 14 of the housing 11 is properly positioned relative to the peritoneum 56, the openings 19 and 20 through the tubular wall of the housing 11 are disposed slightly outwardly of the outer fascia layer 53 of the abdominal wall 51. With the lugs 66 and 67 of the plug 60 seated in respective locating notches 23 and 24 (FIG. 4), the inclined recess 68 is positioned next to the opening 20 in the housing 11. Similarly, the inclined recess 69 is positioned next to the opening 19 in the housing 11. As indicated above, the openings 19 and 20 are preferably formed at an angle to the axis of the bore 17 of the housing 11. The angle of the opening 20 is the same as the angle which the inclined recess 68 forms with the axis of the plug 60, so as to form a continuous slope therewith. Similarly, the opening 19 forms a continuous slope with the inclined recess 69.

A suture snare instrument 80 is used in cooperation with the gripper 10 to pass a suture 81 through two opposed portions of each of the fascia layers 53 and 55. Such a suture snare instrument is described in my U.S. Pat. No. 5,501,692, the disclosure of which is hereby incorporated by reference. Briefly, the suture snare instrument 80 includes an introducer needle 82 having an angled, sharpened tip 83. A flexible wire loop 84 is disposed within portions of the introducer needle 82. The wire loop 84 may be extended from the tip 83 and a first end 85 of the suture 81 passed through the wire loop 84. The wire loop 84 may be retracted into the introducer needle 82 to frictionally capture the first end 85 of the suture 81. The introducer needle 82 is then inserted into the gripper 10 between the arms 63 and 64 of the plug 60. The tip 83 is guided into one of the axially extending passages formed by the cooperation of the tubular wall of the housing 11 with the inclined recesses 68 and 69 formed on the outer surface of the plug 60. For the purposes of illustration, the introducer needle 82 is assumed to be first inserted into the recess 68, along with the first end 85 of the suture 81.

The angled tip 83 of the introducer needle 82 engages the outwardly sloped recess 68 as the suture snare instrument 80 is urged inwardly toward the abdominal cavity. The sloped recess 68 urges the angled tip 83 of the introducer needle 82 outwardly through the opening 20 in the tubular wall of the housing 11 and into the fat layer 52 immediately outward of the outer fascia layer 53 of the abdominal wall 51. The introducer needle 82, extending at an angle to the housing 11, penetrates the fascia layers 53 and 55 at a distance from the puncture in which the gripper 10 is located.

When the introducer needle 82 extends into the abdominal cavity, the wire loop 84 is extended to release the first end 85 of the suture 81. The loop 84 is then retracted back into the introducer needle 82. The suture snare instrument 80 can then be pulled back out of the abdominal cavity and out of the gripper 10, leaving the first end 85 of the suture 81 in the abdominal cavity.

The introducer needle 82 of the suture snare instrument 80 is then passed through the other of the axially extending passages formed by the cooperation of the housing 11 and the inclined recesses 68 and 69 of the plug 60. In the example illustrated in FIG. 5, the introducer needle is inserted into the inclined recess 69. As the suture snare instrument 80 is urged inwardly, the angled tip 83 of the introducer needle 82 engages the body of the plug 60 defining the inclined recess 69. The tip 83 of the introducer needle is thereby urged outwardly through the opening 19 and into the fat layer 52 of the abdominal wall 51 a small distance outwardly of the outer fascia layer 53. The introducer needle 82 penetrates the fascia layers 53 and 55 at a location spaced apart from the puncture through which the gripper 10 extends, and passes into the abdominal cavity. With the tip 83 of the introducer needle 82 extending into the abdominal cavity, the wire loop 84 is extended, and the first end 85 of the suture 81 is inserted through the wire loop 84. If necessary, elongated laparoscopic manipulating tools may be inserted through the axial bore 70 of the plug 60 and into the abdominal cavity to manipulate the end 85 of the suture 81. The wire loop 84 is then retracted into the introducer needle 82 and the suture snare instrument 80 is withdrawn. This causes the first end 85 of the suture 81 to be drawn up through the fascia layers 53 and 55, into the opening 19, along the inclined recess 69 in the plug 60, and out of the gripper 10.

With both ends of the suture 81 extending out of the abdominal wall 51, the gripper 10 is removed by grasping the flange 12 of he housing 11, and pulling the gripper 10 axially outwardly from the puncture through the abdominal wall 51. Note that the helical thread 16 formed on the external surface of the housing 11 sufficiently engages the abdominal wall 51 to prevent the gripper 10 from being accidentally dislodged or expelled by the inert gas. However, the helical thread 16 will not prevent a relatively firm pull from pulling the housing 11 from the abdominal wall 51. The user can then pull the suture 81 out of the gripper 10, and tie a knot (not shown) in the suture 81 that draws the fascia layers 53 and 55 together to close the puncture through which the gripper 10 had extended. Note that the locations at which the suture 81 passes through the fascia layers are sufficiently remote from the puncture site that a firm knot may be tied without pulling the suture 81 through the tissue into the puncture. The knot will be tied within the fat layer 52, which is closed up over the knot along with the skin 50 in a conventional manner.

Figure 7:
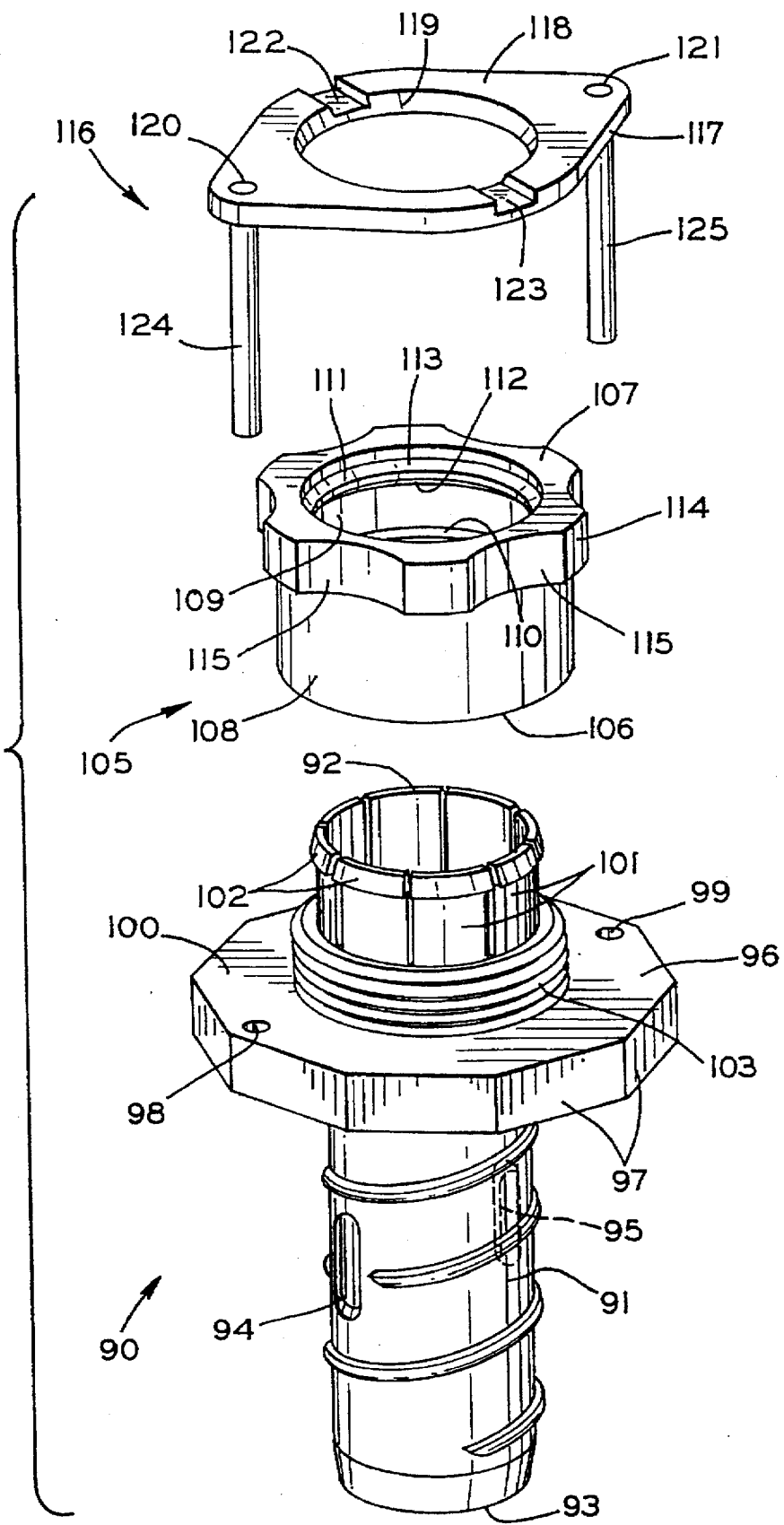
FIG. 7 is an exploded perspective view of a second embodiment of a gripper in accordance with this invention, wherein the gripper is provided with a threaded gripping structure.

FIG. 7 illustrates a second embodiment of a gripper 90 in accordance with this invention. The gripper 90 is generally similar in structure to the gripper 10, except as noted below. The gripper 90 includes a tubular housing 91 having an outer end 92 and an inner end 93. A pair of opposed openings 94 and 95, similar to the openings 19 and 20 of the gripper 10, are formed through the tubular wall of the housing 11.

A radially outwardly extending flange 96 is formed on the housing 91 intermediate the outer end 92 and the inner end 93. In the illustrated embodiment, a plurality of flats 97 are formed on the radially outer surface of the flange 96 to provide a relatively non-slip surface for gripping and turning the gripper 90. A pair of opposed recesses 98 and 99 are formed on the outer face 100 of the flange 95. The recesses 98 and 99 are preferably longitudinally aligned with the two opposed openings 94 and 95 in the housing 91.

The outer end 92 of the gripper 90 is provided with a plurality of longitudinally extending fingers 101 adapted to be bent radially inwardly to grip the trocar 40 (FIG. 1) or the plug 60 (FIG. 4). Preferably, the free end of each finger 101 is provided with an inclined cam surface 102 on the radially outer surface thereof, the purpose of which will be explained below. A threaded section 103 is formed on the outer surface of the housing 91 intermediate the fingers 101 and the flange 96.

The gripper 90 also includes an annular locking nut 105. The locking nut 105 has a first end 106, a second end 107, an outer surface 108 and an inner surface 109. A threaded section 110 is formed on the inner surface 109 of the locking nut 105 adjacent the first end 106. The threaded section 110 is adapted to engage the threaded section 102 of the housing 91.

A circumferential, radially inwardly extending rib 111 is formed on the inner surface 109 of the locking nut 105, adjacent the second end 107 thereof. The rib 111 includes a camming surface 112 which is inwardly inclined toward the second end 107. As will be further explained below, the camming surface 112 is adapted to engage the camming surfaces 102 of the fingers 101 of the housing 91. The rib 111 also includes a second surface 113 which is preferably inwardly inclined toward the first end 106 to facilitate the insertion of the trocar 40 and the plug 60 through the locking nut 105.

A radially outwardly extending flange 114 is formed on the outer surface 108 Of the locking nut 105. The flange 114 is preferably provided with a relatively non-slip surface on the radially outer surface thereof, as by the illustrated longitudinally extending grooves 115.

Figure 8:
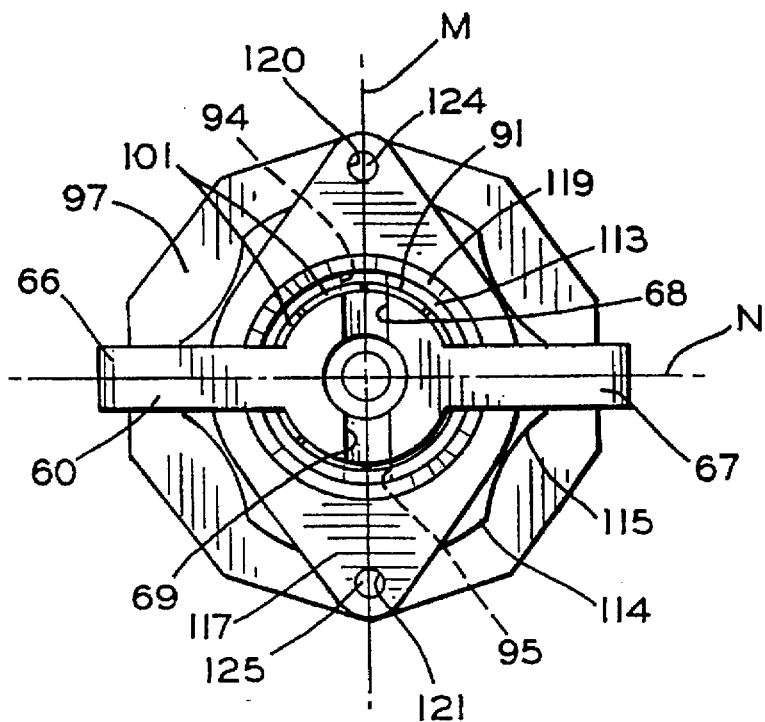
FIG. 8 is an end elevational view of the assembled gripper illustrated in FIG. 7.

The gripper 90 also includes a cap 116. The cap includes a flat body 117 having an outer surface 118 and an opposed inner surface (not shown). The body 117 is preferably diamond-shaped in outline, and thus defines a major axis M along the length thereof, and a minor axis N along the width thereof, perpendicular to the major axis M (as seen in FIG. 8). The body 117 is provided with a central opening 119. The central opening 119 is preferably inwardly inclined away from the outer surface 118, to aid in inserting the trocar 40 or plug 60 through the central opening 119. Additionally, a pair of smaller openings 120 and 121 are formed on the major axis M of the body 117, adjacent the ends thereof.

A pair of locating notches 122 and 123 are formed in the outer surface 118 of the body 117, extending from the outer periphery of the body 117 to the central opening 119. The locating notches 122 and 123 lie on the minor axis N (FIG. 8) of the body 117. The locating notches 122 and 123 are adapted to receive the lugs 66 and 67 formed on the plug 60. The locating notches 122 and 123 thus function in a manner similar to the locating notches 23 and 24 of the gripper 10 to axially and rotationally orient the plug 60.

The body 117 of the cap 116 is supported on a pair of longitudinally extending rods 124 and 125 which are fixed at respective first ends in the openings 120 and 121, and at respective second ends in the recesses 98 and 99 formed in the flange 96 of the housing 91. The rods 124 and 125 may be fixed in the recesses 98 and 99 and the openings 120 and 121 by any conventional means such as press fitting or with an adhesive. The rods 124 and 125 may also be formed integrally with the body 117 of the cap 116, which is preferably formed from a rigid plastic material. The rods 124 and 125, being fixed in the recesses 98 and 99, are longitudinally aligned with respective openings 94 and 95 formed through the housing 91. The locating notches are thus correctly positioned to orient the plug 60 with the inclined recesses 68 and 69 thereof correctly positioned relative to the openings 94 and 95 in the housing 91, as illustrated in FIG. 8.

During assembly of the gripper 90, the locking nut 105 is passed over the outer end 92 of the housing 91 and the threaded section 110 of the locking nut 105 is loosely screwed onto the threaded section 103 of the housing 91. The cap 116 is then fixed into place as described above. Preferably the length of the rods 124 and 125 will be such that after the cap 116 is assembled onto the housing 91, the locking nut 105 will be captured on the outer end 92 of the housing 91.

While the locking nut 105 is only loosely screwed onto the housing 91, the trocar 40 and the plug 60 may be freely moved within the gripper 90. In order to cause the gripping fingers 101 to bend radially inwardly to grip the trocar 40 or the plug 60, the locking nut 105 is screwed more tightly onto the outer end 92 of the housing 91, advancing the locking nut 105 toward the flange 96 of the housing 91. This causes the cam surface 112 of the rib 111 on the locking nut 105 to engage the cam surfaces 102 of the fingers 101, which cooperate to bend the fingers 101 radially inwardly. As will be appreciated by referring to FIG. 8, the diamond shape of the body 117 of the cap 116 permits ready access to the flange 114 on the locking nut 105. Thus the flange 114 may be easily gripped and turned to move the locking nut 105 toward or away from the flange 96 of the housing 91, causing the fingers 101 respectively to be bent inwardly, or to spring outwardly toward their relaxed state positions.

Figure 9:
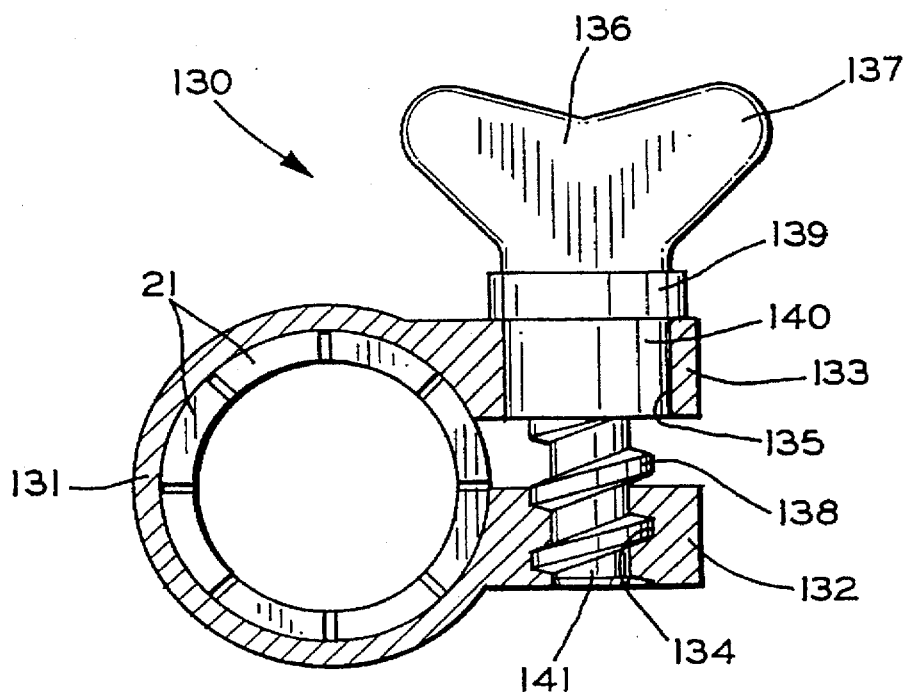
FIG. 9 is an end elevational view, partly in section, of a third embodiment of a gripper in accordance with this invention, wherein the gripper is provided with a screw clamp gripping structure.

FIG. 9 illustrates a third embodiment of a gripper 130 in accordance with this invention. The gripper 130 is identical in structure to the gripper 10, except the structure of the clamp encircling the gripping fingers 21, and the same reference numbers will be used to refer to identical parts. The clamp 131 encircling the fingers 21 of the gripper 130 is preferably formed of a resilient plastic material. The clamp 131 is formed into a circular shape, with a first end having a single radially outwardly extending lug 132. The second end of the clamp 131 is formed with a second radially outwardly extending lug 133. The diameter of the clamp 131, may be reduced by moving the lug 132 toward the lug 133.

The lug 132 is provided with a threaded bore 134, which is aligned with a smooth bore 135 through the lug 133.

The gripper 130 also includes a thumbscrew 136 which cooperates with the clamp 131. The thumbscrew 136 includes a finger grip 137 and a shaft 138. A thrust collar 139 extends radially outwardly between the finger grip 137 and the shaft 138. The shaft 138 is provided with a smooth bearing section 140 adjacent the thrust collar 139 and a threaded section 141 at the free end thereof.

The thumbscrew 136 is inserted through the bore 135 in the lug 133 and twisted so that the threaded portion 141 of the shaft 138 engages the threaded bore 134 of the lug 132. The bearing section 140 supports the thumbscrew within the bore 135 of the lug 133.

To contract the clamp 131 and bend the gripping fingers 21 radially inwardly, the fingergrip 137 of the thumbscrew 136 is gripped by the finger and thumb of a user (not shown) and twisted to screw the shaft 138 into the threaded bore 134 of the lug 132. This causes the thrust collar 139 to bear against the lug 133, causing the lug 133 to advance toward the lug 132 and decreasing the diameter of the clamp 131. To allow the gripping fingers 21 to move radially outwardly to their relaxed state, the user twists the thumbscrew 136 in the opposite direction. This causes the thumbscrew 136 to move outwardly from the threaded bore 134 of the lug 132, and allows the lug 133 to move with the thrust collar.

Figures 10, 11, 12:
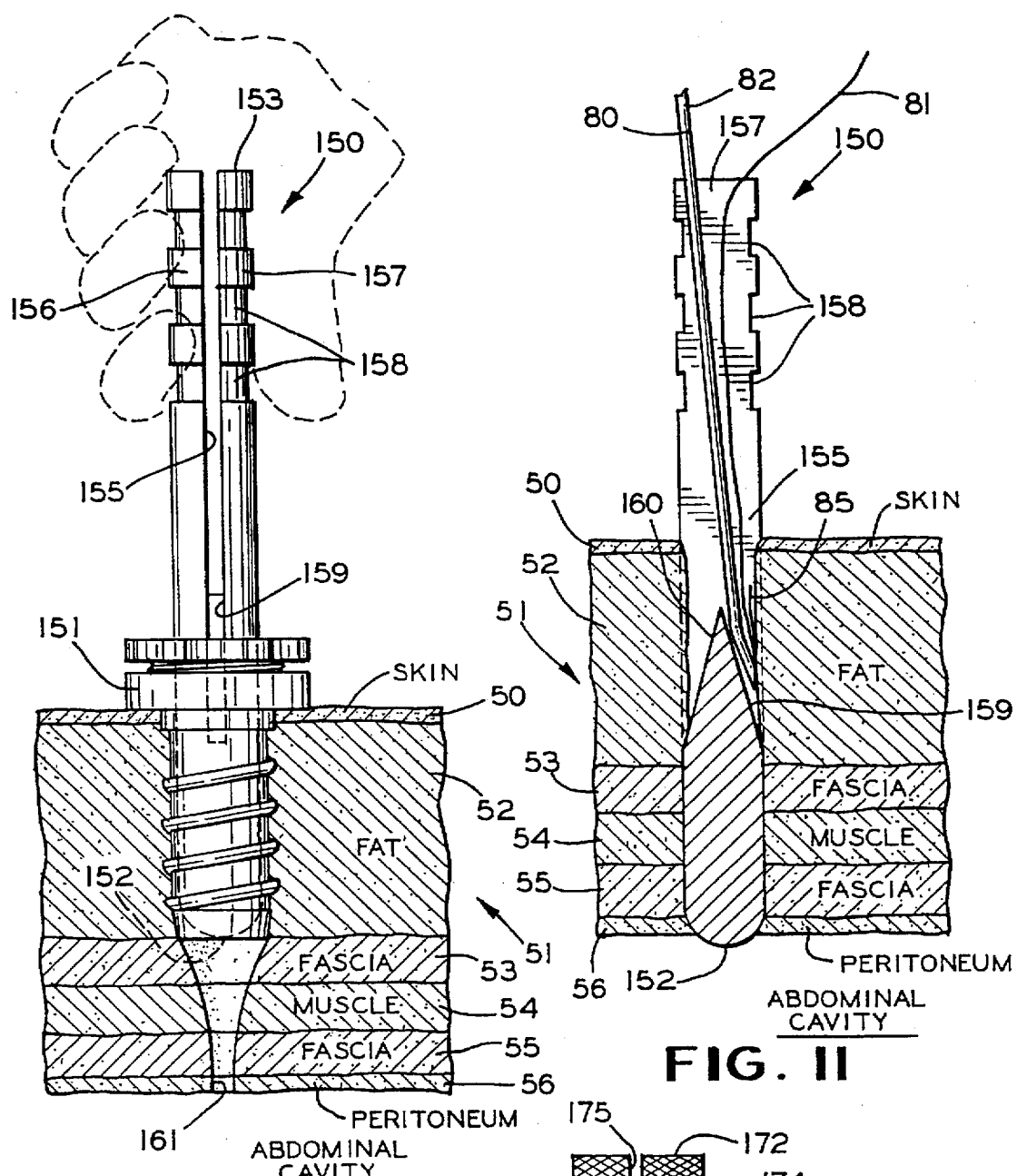
FIG. 10 is a front elevational view of a second embodiment of a plug in accordance with this invention partially inserted into a conventional trocar gripper.
FIG. 11 is a sectional elevational view of the plug illustrated in FIG. 10 with the trocar gripper removed.
FIG. 12 is a side elevational view of a third embodiment of a plug in accordance with this invention.

FIGS. 10 and 11 illustrates second embodiment of a removable plug 150 in accordance with this invention. The plug 150 is adapted to be used with the grippers 10 or 90 described above, and may also be used with a conventional gripper 151 as illustrated. The plug 150 is generally cylindrical and has a first end 152 and a second end 153. The second end 153 includes a central slot 155 extending transversely through the plug 150 to form a pair of axially extending parallel arms 156 and 157. A plurality of spaced apart, circumferentially extending grooves 158 are formed adjacent the second end 153 of the plug 150, interrupted only by the central slot 155. The grooves 158 provide a relatively slip-resistant finger grip on the arms 156 and 157, adjacent the second end of the plug 150.

As is most clearly seen in FIG. 11, the central slot 155 provides communication with a pair of opposed recesses 159 and 160 formed in the outer surface of the plug 150. The recess 159 extends axially from the central slot 155 at the longitudinal axis defined by the plug 150, to a point intermediate the first end 152 and the second end 153 of the plug 150. The recess 159 is outwardly inclined toward the first end 152 of the plug 150. The recess 160 is formed on the opposite side of the plug 150 from the recess 159. The recess 160 is similarly outwardly inclined from the central slot 155 toward the first end 152 of the plug 150 to a point intermediate the first end 152 and the second end 153. As will be further explained below, the recesses 159 and 160 preferably extend to a point approximately two and a half centimeters from the first end 152. As with the plug 60, the plug 150 is preferably molded from a rigid plastic material.

In operation, a conventional trocar such as the trocar 40 illustrated in FIGS. 1, 2 and 3 is used to create a puncture 161 through the abdominal wall 51 of a patient. The gripper 151 is used to secure the trocar guide tube 41 of the trocar 40 in the conventional manner. When the user desires to suture the puncture 161, the gripping structure of the gripper 151 is loosened and the trocar 40 is removed, leaving the gripper 151 in the puncture 161.

The plug 150 may be quickly inserted into the gripper 151 to prevent the rapid escape of inert gas from the abdominal cavity. Typically, the plug 150 will be inserted by grasping the second end thereof with the fingers and thumb of a hand, such as shown in dotted lines in FIG. 10. As indicated above, the grooves 158 provide a relatively non-slip surface for grasping the plug 150.

The plug is inserted into the abdominal wall 51 until the recesses 159 and 160 are slightly outward of the outer fascia layer 53. As indicated above, the distance from the peritoneum to the outer fascia layer 53 is generally in the range of two centimeters, regardless of the thickness of the fat layer 52. As also indicated above, the recesses 159 and 160 preferably terminate approximately two and a half centimeters from the first end 152 of the plug 150. Thus, when the first end 152 of the plug 150 is generally even with the peritoneum 56, the recesses 159 and 160 will be at the desired distance outward of the outer fascia layer 53 in a typical patient. Note that even when the gripper 151 is of insufficient length to extend through the abdominal wall 51 of the patient, the plug 150 can be positioned axially within the puncture 161 as desired.

Once the plug 150 is properly positioned within the puncture 161, the user removes the gripper 151, either by unscrewing it or by pulling it axially from the abdominal wall 51, while the plug 150 is held in place. Once free of the abdominal wall 51, the gripper 151 may be slid off the second end 153 of the plug 150, with the user changing grips on the plug 150 as needed to accomplish the maneuver while holding the plug 150 in place.

With the gripper 151 removed, the tissues of the abdominal wall 51 will close in about the plug 150, possibly extending slightly into the central slot 155 and the recesses 159 and 160 as shown in FIG. 11. However, the recesses 159 and 160 and the central slot 155 should be sufficiently narrow that the tissue does not intrude substantially into the recesses 159 and 160 and the central slot 155. Thus the central slot 155 and the recesses 159 and 160 provide communication between the second end 153 of the plug 150 and the abdominal wall 51 slightly outward of the outer fascia layer 53. The introducer needle 82 of the suture snare instrument 80 may then be used to pass a first end 85 of the suture 81 through one of the recesses 159 and 160 and thence through the fascia layers 53 and 55 into the abdominal cavity as described above. The suture 81 is released, and the suture snare instrument 80 withdrawn and then passed through the other of the recesses 159 and 160, and the fascia layers 53 and 55 into the abdominal cavity. The suture snare instrument 80 is then used to grasp the first end 85 of the suture 81 and pull it from the abdominal cavity through the fascia layers 53 and 55, and out of the plug 150. The plug 150 is then removed from the puncture 161 and the ends of the suture 81 tied in a conventional manner.

FIG. 12 illustrates a third embodiment of a plug 170 in accordance with this invention. The plug 170 is designed for insertion into a puncture through multiple layers of tissue, for example in an abdominal wall 51. Unlike the previously described plugs 50 and 150, the plug 170 is designed to be inserted into a puncture without a trocar gripper installed therein. The plug 170 is generally conical in shape, having a first end 171 and a second end 172. Helical threads 173 are formed on the outer surface of the plug 170 between the first end 171 and the second end 172. The second end 172 preferably is provided with a gripping area or portion 174 integrally formed thereon. The gripping portion 174 may be of any suitable shape which facilitates grasping and turning the plug 170, such as the illustrated knurled cylindrical shape. The second end 172 includes a central slot 175 extending transversely through the plug 170, including the gripping portion 174, to form a pair of axially extending parallel arms 176 and 177.

In a manner similar to the central slot 155 of the plug 150, the central slot 175 provides communication with a pair of opposed recesses 178 formed in the outer surface of the plug 170 (only one of which is shown). The recesses 178 extend axially from the central slot 175 at the longitudinal axis defined by the plug 170, to opposed points intermediate the first end 171 and the second end 172 of the plug 170. Each recess 178 is outwardly inclined toward the first end 171 of the plug 170. Preferably, the entire plug 170 is molded from a rigid plastic material.

As briefly discussed above, the plug 170 designed for insertion into a puncture such as that which may be made by the trocar 40 illustrated in FIGS. 1, 2, and 3, to facilitate suturing thereof. However, it should be recognized that suturing of other types of puncture wounds may be facilitated by the use of the plug 170. In any case, the plug 170 may be inserted into the puncture after all objects holding the puncture open, such as a trocar gripper, are removed, and the tissue surrounding the puncture has closed inwardly on the puncture.

The user can grasp the plug 170 using the gripping portion 174 and insert the pointed first end 171 of the plug 170 into the outer end of the puncture. The plug 170 may then be moved axially into the puncture to the desired position by pushing and turning the plug so that the threads 173 cooperate with the surrounding tissue to screw the plug 170 into the puncture. The conical shape of the plug 170 expands the puncture radially as the plug 170 penetrates into the puncture to provide access to the inner portions of the puncture. The user can thus position the recesses 178 of the plug at a desired location within the puncture, such as slightly outward of the outer fascia layer in the abdominal wall of a patient.

The central slot 175 and the recesses 178 provide communication from the second end 172 of the plug to the desired location within the puncture for suturing. A user Can then use the suture snare instrument 80 to pass a suture through the tissue layers, especially the fascia layers, on opposite sides of the puncture, in the manner described above. After the plug 170 is removed, a knot can be tied in the suture to close the puncture.

Figure 13:
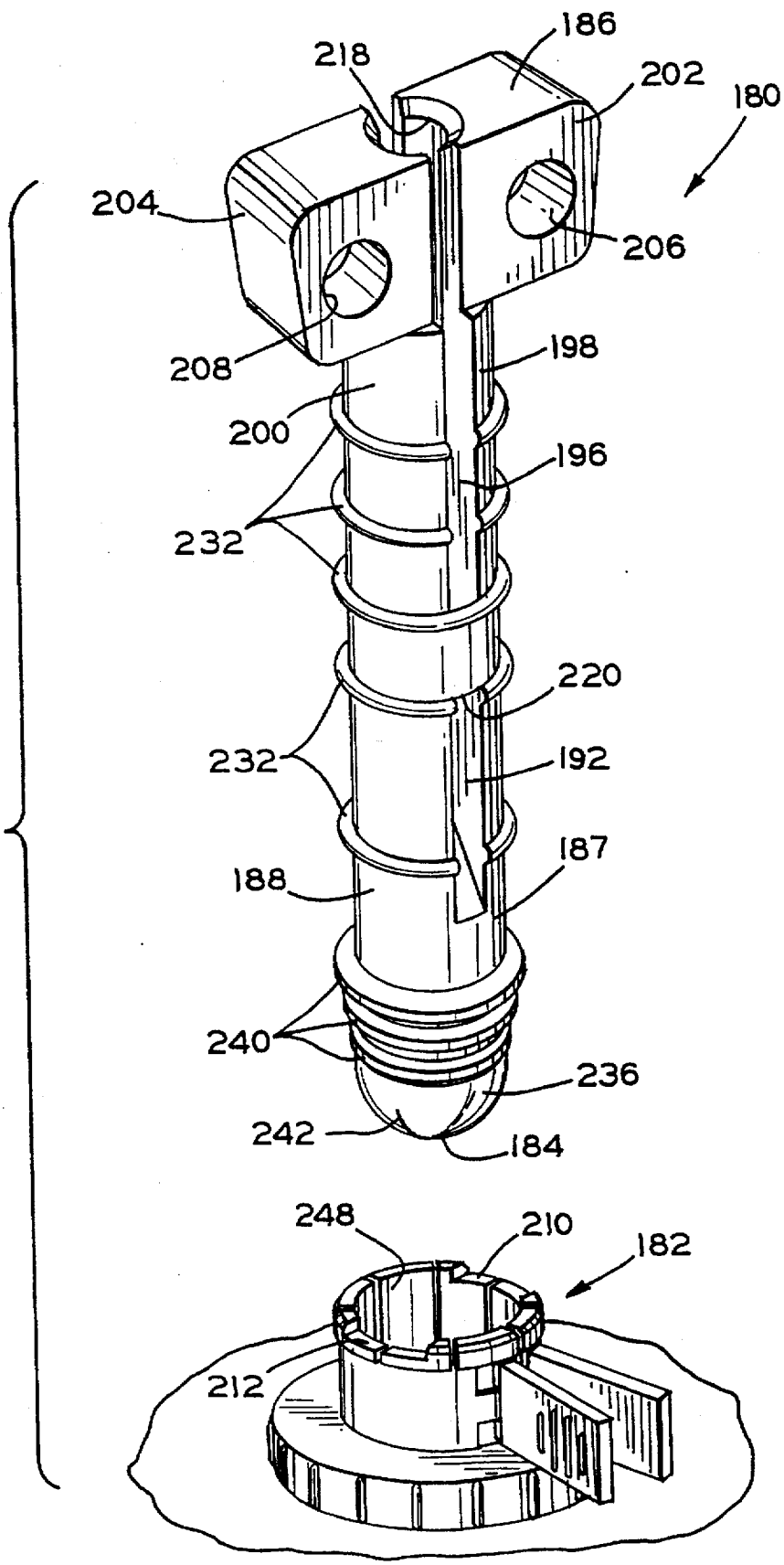
FIG. 13 is an exploded perspective view of a fourth embodiment of a plug add a gripper in accordance with this invention.
Figure 14:
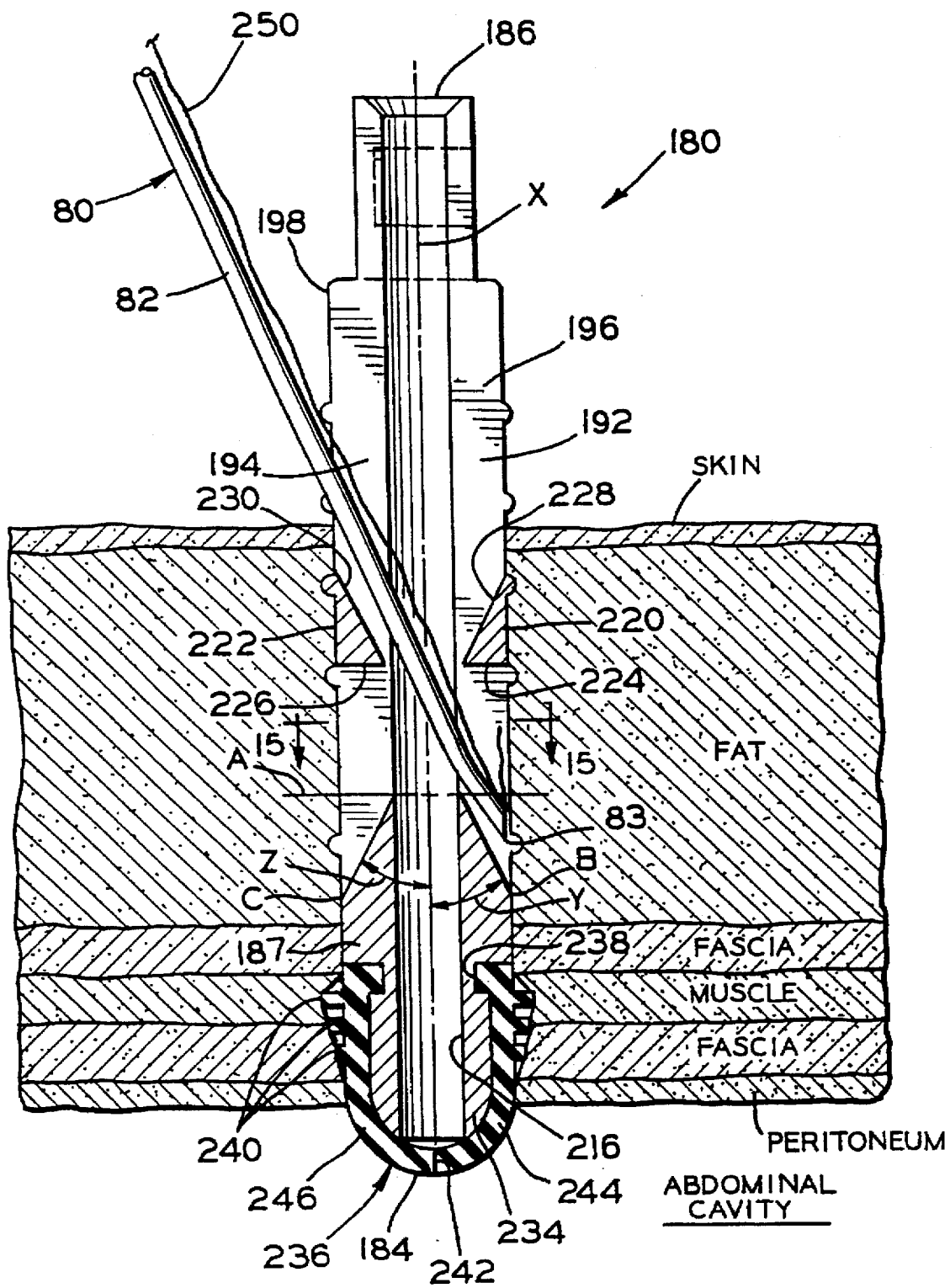
FIG. 14 is a sectional view of the plug illustrated in FIG. 13 shown inserted directly into the abdominal of a patient.

FIGS. 13 and 14 illustrate a fourth embodiment of a plug 180 in accordance with this invention. The plug 180 is adapted to be used with a gripper 182, as shown in FIG. 13, which is similar in structure and function to the gripper 10 described above. The plug 180 can also be used with any suitable gripper, such as the grippers 90 and 151. FIG. 13 shows the plug 180 prior to insertion into the gripper 182. The plug 180 is also designed for direct insertion into a puncture of a patient through multiple layers of tissue, as shown in FIG. 14.

The plug 180 has distal first end 184 and a proximal second end 186, and has a body 187 with a generally cylindrical outer surface 188. As best seen in FIG. 14, the body 187 of the plug 180 is provided with a pair of recesses 192 and 194 formed in the outer surface 188 of the plug 180. The recess 192 is formed on the opposite side of the plug 180 from the recess 194. The recesses 192 and 194 extend axially from the second end 186 of the plug 180 to respective points in a plane "A". The plane A is defined perpendicular to the central longitudinal axis X of the plug 180 and is located intermediate the first end 184 and the second end 186. From the point in plane A to a point "B" between the plane A and first end 184, the recess 192 is formed at an angle "Y" to the longitudinal axis X of the plug 180. Thus, the recess 192 has a decreasing depth toward the first end 184 from the plane A to the point B. The recess 194 similarly extends axially from the second end 186 of the plug 180 to a point in the plane A. The recess 194 is outwardly sloped from that point in the plane A toward a point "C" between the plane A and the first end 184 of the plug 180. The recess 194 forms an angle "Z" to the axis X in the outwardly sloped portion of the recess 194. Preferably, the angles Y and Z are equal.

Preferably, the recesses 192 and 194 are sufficiently deep so that portions thereof combine to form a single slot 196 extending through a portion of the body 187 of the plug 180, thereby separating two parallel arms 198 and 200. The arms 198 and 200, defining the slot 196, extend from the plane A toward the second end 186 of the plug 180. Each of the arms 198 and 200 is provided with a radially outwardly extending lug, 202 and 204, respectively, at the proximal end thereof. Preferably, each lug 202 and 204 has a cavity 206 and 208, respectively, which helps to maintain a generally constant wall thickness for the plug 180 to aid in the molding process. The lugs 202 and 204 cooperate with respective locating notches 210 and 212 formed in a housing 214 of the gripper 182, to orient the plug 180 relative to the gripper 182. Thus, the lugs 202 and 204 and the corresponding notches 210 and 212 function in a manner similar to the lugs 66 and 67 of the plug 60 and corresponding locating notches 23 and 24 of the gripper 10 described above when the plug 180 is used without a gripper, as illustrated in FIG. 14. The lugs 202 and 204 prevent the entire plug 180 from being inserted through a puncture in an abdominal wall by contacting the outer layer of skin and aid in properly positioning the plug 180.

Figure 15:
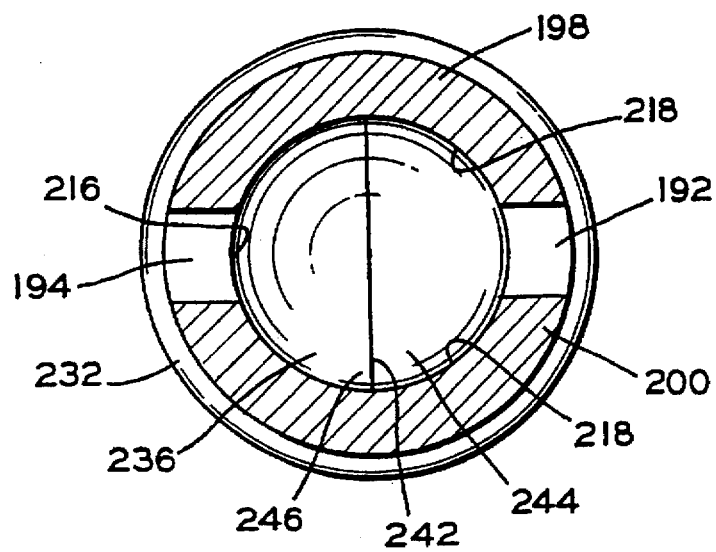
FIG. 15 is a view taken along the lines 15—15 in FIG. 14.

Referring now to FIG. 14 and 15, the plug 180 is preferably provided with a longitudinal bore 216 extending longitudinally through the plug 180 from the first end 182 to the second end 184. The bore 216 permits insertion of laparoscopic surgical instruments through the plug 180. If the diameter of the bore 216 is larger than the width of the recesses 192 and 194, and the recesses 192 and 194 are sufficiently deep to communicate with the bore 216, a respective semicylindrical notch 218 can be formed in the opposed faces of the arms 198 and 200 between the plane A and the second end 186.

The plug 180 is further preferably provided with a pair of reinforcement segments 220 and 222 formed at the approximate mid-point of the plug 180. The segments 220 and 222 extend from the arm 198 to the arm 200, thereby connecting the arms 198 and 200 together. The segments 220 and 222 have a generally triangular cross-section, as shown in FIG. 14. The segments 220 and 222 have laterally extending first sides 224 and 226, respectively, which face the first end 184 and extend laterally with respect to the axis X of the plug 180. The segment 220 has a second sloped side 228 which slopes inwardly at an angle with respect to the axis X of the plug 180 and more closely approaches the axis X toward the first end 184 of the plug 180. Similarly, the segment 222 has a second sloped side 230 which slopes inwardly at an angle with respect to the axis X of the plug 180 and more closely approaches the axis X toward the first end 184. The segments 220 and 222 function to resist bending of the arms 198 and 200 toward one another when subjected to external pressure. Such external pressure would be present, for example, if the plug 180 is inserted directly into a puncture opening (without the use of the gripper 182), as is illustrated in FIG. 14. As the abdominal wall tries to close in the puncture opening, the segments 220 and 222 prevent the arms 198 and 200 from moving toward one another, thus maintaining the slot 196 open to receive surgical instruments. It is expected that normally only one pair of reinforcement segments 220 and 222 will be provided. However, depending upon the length and diameter of the plug 180 and the materials from which the plug 180 is made, more or fewer reinforcement segments may be provided.

The plug 180 is also preferably provided with a plurality of ribs 232 formed on the outer surface 188 thereof. The purpose of the ribs 232 will be described below As best seen in FIG. 14, the first end 184 of the plug 180 includes an extension 234 extending axially from the distal end of the body 187. The extension 234 includes a reduced diameter portion and an enlarged head portion so that the extension 234 is generally mushroomed-shaped. A cupped shaped elastomeric seal 236 which is positioned over the mushroom-shaped extension 234 of the body 187. Preferably, the seal 236 is made of an elastomeric material, such as latex rubber. The seal 236 is retained on the extension 234 by an inwardly extending flange 238 formed about the rim thereof which engages the reduced diameter portion of the extension 234. The seal 236 is prevented from moving therefrom by the enlarged head portion of the extension 234. Preferably, the seal 236 is further fixed to the extension 234 by a suitable adhesive. The seal 236 is preferably provided with at least one and more preferably provided with a plurality of external sealing rings 240 formed as radially outwardly extending, circumferential flanges on the outer surface of the seal 236. Note that, preferably, the rings 240 are of different diameters. Of each pair of adjacent rings 240, the rings 240, in a direction toward the second end 186 of the plug 180, will be of greater diameter than the other ring 240 of the adjacent pair.

Referring to FIGS. 14 and 15, the seal 236 is provided with a central incision 242 formed in a central portion of the seal 236. The incision 242 divides the central portion of the seal 236 into two flaps 244 and 246 which resiliently covers the bore 216 of the plug 180 and allows passage of a surgical instrument inserted through the bore 216. The incision 242 generally seals the distal end of the bore 216 when a surgical instrument is not inserted therethrough. Of course, the incision 242 can be of any suitable shape, such as a single slit described above or a cross-shaped slit.

In operation, the plug 180 can be used with the gripper 182 which is inserted within the abdominal cavity, similar to the operation of the plug 60 and the gripper 10 described above. The rings 240 on the seal 236 of the plug 180 provide for a sealing engagement between the plug 180 and an inner axial bore 248 of the gripper 182. Preferably, the gripper 182 has a pair of openings (not shown, but similar to the openings 19 and 20 in the gripper 10) which align with the recesses 192 and 194, in the portion thereof between the segments 220 and 222 and the first end 184 of the plug 180. In another suitable arrangement, the housing of the gripper would be relatively short so that when the plug 180 was inserted into the gripper, the sloped portions of the recesses 192 and 194 would extend beyond the distal end of the gripper.

The plug 180 can also be used without the gripper 182. For example, when the surgeon desires to suture a puncture, the trocar gripper 182 is first removed from the abdominal wall. Immediately, the surgeon places a gloved finger over the puncture opening to retain the pneumoperitoneum. The plug 180 is then inserted in the puncture through the abdominal wall with the assistance of a laparoscopic visualization device, so that the first end 184 of the plug 180 is generally aligned at the surface of the peritoneum, as shown in FIG. 14. The ribs 232 of the plug 180 engage the abdominal wall and help to prevent the plug 180 from being ejected from the puncture by the pressure of the insufflation gas within the abdominal cavity. A suture 250 is then "loaded" onto the introducer needle 82 of the suture snare instrument 80, as shown in FIG. 14, so that an end of the suture 250 is temporarily held near the sharpened tip 83 of the introducer needle 82. The introducer needle 82 is then inserted axially through the slot 196 of the plug 180. The sharpened tip 83 of the suture snare instrument 80 is then advanced through the slot 196 to engage the sloped surface of the recess 192 or 194 between the associated segments 220 (or 222 if in the recess 194) and the point B (or the point C if in the recess 194), as shown in FIG. 14. The sharpened tip 83 is then inserted through the fascia layers into the abdominal cavity. The suture 250 is then released and the introducer needle 82 is withdrawn from the slot 196 of the plug 180. The introducer needle 82 is then reinserted axially through the slot 196 of the plug 180 and the sharpened tip 83 is advanced to engage the opposite sloped surface of the recess 194 or 192. The introducer needle 82 is then inserted through the fascia into the abdominal cavity. With the help of a grasper (not shown) or a needle holder (not shown), the free end of the suture 250 within the abdominal cavity is captured by the suture snare 82. The introducer needle 82 is withdrawn back through the fascia and the slot 196 of the plug 180. The suture 250 is then released, thereby completing the placement of the suture 250. After all the desired sutures are in place, the sutures are tightened while the plug 180 is removed from the puncture opening. After the plug 180 has been removed, the sutures are then tightened under direct visualization.

Note that a plurality of plugs similar to the plug 180 may be provided, each having a different length to accommodate patients with different abdominal wall thicknesses.

Figures 16, 17:
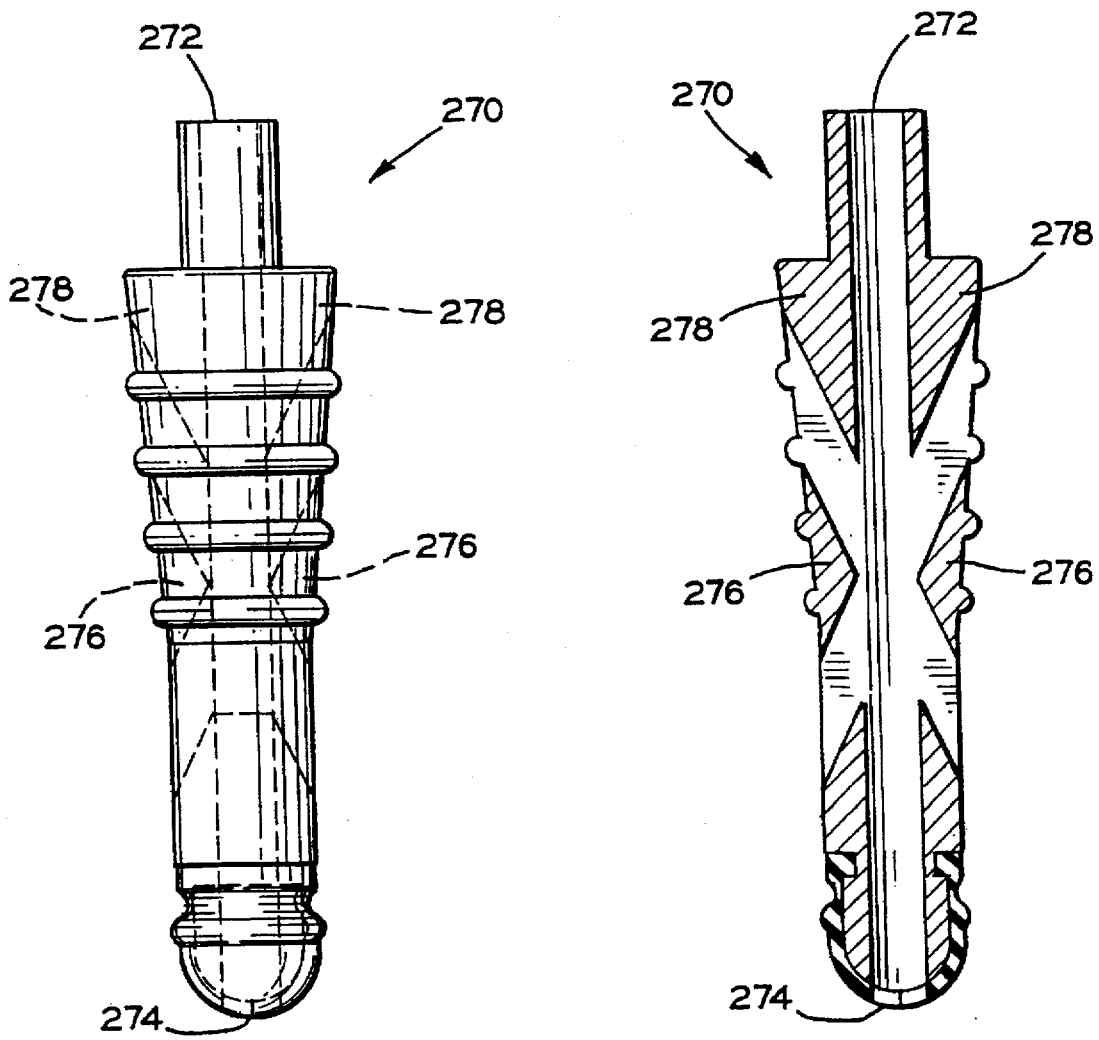
FIG. 16 is an elevational view of a fifth embodiment of a plug in accordance with the invention.
FIG. 17 is a sectional view of the plug illustrated in FIG. 16.

FIGS. 16 and 17 illustrate a fifth embodiment of a plug 270 having a first end 272 and a second end 274. The plug 270 is provided with a first pair of reinforcement segments 276 disposed generally at the mid-point of the plug 270, as best seen in FIG. 16. The plug 270 also has a second pair of reinforcement segments 278 disposed generally at the second end 274 of the plug 270.

In accordance with the provisions of the patent statutes, the principle and mode of operation of the present invention have been explained and illustrated in the preferred embodiment, however, it will be understood that the present invention may be practiced otherwise than as specifically explained and illustrated without departing from its spirit or scope.

What is claimed is:

1. An apparatus for facilitating suturing of minimally invasive surgery puncture wounds comprising:

a body defining a longitudinal axis, said body having a first end and a second end, said first end being adapted to be inserted into a puncture wound, said body including a pair of arms extending generally parallel to said axis from said second end to a point intermediate said first end and said second end, said pair of arms defining a recess therebetween, a portion of said recess most adjacent said first end being inclined so as to have decreasing depth toward said first end; and a reinforcement segment extending between said pair of arms.

2. The apparatus for facilitating suturing defined in claim 1, wherein said body defines a pair of opposing recesses cooperating to form a single slot defined between said arms.

3. The apparatus for facilitating suturing defined in claim 1, wherein said body defines a longitudinal axial bore therethrough.

4. The apparatus for facilitating suturing defined in claim 3, wherein said axial bore is in communication with said recess.

5. The apparatus for facilitating suturing defined in claim 3 further comprising a seal operatively coupled to said body to selectively seal said axial bore through said body.

6. The apparatus for facilitating suturing defined in claim 5, wherein said seal comprises latex rubber.

7. The apparatus for facilitating suturing defined in claim 5, wherein said seal has an incision through a central portion of said seal which is aligned with said axial bore, said incision defining a pair of flaps.

8. The apparatus for facilitating suturing defined in claim 5, wherein said seal has a plurality of circumferentially extending rings formed on the outer surface thereof.

9. The apparatus for facilitating suturing defined in claim 5, wherein said first end of said body includes an extension with an enlarged end portion, and said seal is operatively coupled to said extension.

10. The apparatus for facilitating suturing defined in claim 1 further comprising a lug extending radially outwardly from one of said arms.

11. The apparatus for facilitating suturing defined in claim 1, wherein said segment has a first end fixed to one of said pair of arms between said second end of said body and said point intermediate said first and said second end, said segment having a second end fixed to the other of said pair of arms between said second end of said body and said point intermediate said first and second end.

12. The apparatus for facilitating suturing defined in claim 1, wherein said segment has a first side which extends perpendicular to said axis.

13. The apparatus for facilitating suturing defined in claim 12, wherein said segment has a second side which slopes inwardly toward at an angle with respect to said axis and has an increasing depth toward said second end of said apparatus.

14. The apparatus for facilitating suturing defined in claim 1, further comprising a plurality of ribs formed on said outer surface of said apparatus, said ribs being adapted to removably engage body tissue defining a puncture wound.

15. An apparatus for facilitating suturing of minimally invasive puncture wounds, said apparatus comprising:

a body having a generally cylindrical shape defining a longitudinal axis, said body defining a first end of said apparatus, said body defining a longitudinal axial bore therethrough;

a pair of arms extending from said body to define a second end of said apparatus;

an outer surface having a longitudinally extending recess formed therein and positioned between said pair of arms, said recess extending from said second end of said apparatus to a first plane, said first being perpendicular to said longitudinal axis of said apparatus and located intermediate said first and second ends, said apparatus and inclined toward said outer surface, said sloped surface extending from said first plane to a first point located on said outer surface of said apparatus, wherein said first point is located intermediate said first plane and said first end of said apparatus;

reinforcement segments extending between said pair of arms;

a plurality of ribs formed on said outer surfaces;

a lug extending radially outwardly from one of said arms; and a seal operatively coupled to said first end of said apparatus, said seal covering said longitudinal axial bore, said seal having an incision in a central portion of said seal, said incision defining a pair of flaps.

16. An apparatus for facilitating suturing of minimally invasive surgery puncture wounds, said apparatus comprising;

a body having first and second ends;

an outer surface of said body having a pair of opposed recesses formed therein, said pair of recesses extending from said second end of said body to a point intermediated said first and said second end;

a pair of arms extending from said body to define the second end of said body;

a plurality of body tissue engaging ribs formed on said outer surface; and pl a pair of lugs extending radially outwardly from said second end of said apparatus.

17. The apparatus for facilitating suturing defined in claim 16 further including an elastomeric seal attached to said first end of said body.

18. The apparatus for facilitating suturing defined in claim 16 further including a reinforcement segment extending between said pair of arms.

19. The apparatus for facilitating suturing defined in claim 18, wherein each of said pair of arms has a curved inner facing wall, said wall defining a portion of an axial bore extending through said body.

* * * * *

UNITED STATES PATENT AND TRADEMARK OFFICE
CERTIFICATE OF CORRECTION

PATENT NO. : 5,716,369
DATED : February 10, 1998
INVENTOR(S) : Erol D. Riza It is certified that error appears in the above-identified patent and that said Letters Patent is hereby corrected as shown below:

Column 17, Claim 11, Line 7,    after "and", insert -- said --.

Column 17, Claim 13, Line 3,    after "inwardly", delete "toward".

Column 18, Claim 15, Line 12,    after "said first", insert -- plane --.

Column 18, Claim 15, Line 14,    after "ends,", insert -- said recess having a sloped surface formed at an angle to said longitudinal axis of --.

Column 18, Claim 15, Line 22,    after "outer", change "surfaces" to -- surface --.

Column 18, Claim 16, Line 12,    after "and", delete "pl".

Signed and Sealed this

Fourth Day of August, 1998

*Attest:*

*Attesting Officer*

BRUCE LEHMAN
*Commissioner of Patents and Trademarks*